(12) United States Patent
Krimsky et al.

(10) Patent No.: US 9,539,083 B2
(45) Date of Patent: Jan. 10, 2017

(54) DEVICES AND METHODS FOR STENTING AN AIRWAY

(71) Applicant: Merit Medical Systems, Inc., South Jordan, UT (US)

(72) Inventors: William Krimsky, Owings Mills, MD (US); Zeke Eller, Plano, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 193 days.

(21) Appl. No.: 14/550,455

(22) Filed: Nov. 21, 2014

(65) Prior Publication Data

US 2015/0081035 A1    Mar. 19, 2015

Related U.S. Application Data

(62) Division of application No. 13/656,061, filed on Oct. 19, 2012.

(Continued)

(51) Int. Cl.
*A61F 2/06* (2013.01)
*A61F 2/04* (2013.01)
(Continued)

(52) U.S. Cl.
CPC . *A61F 2/04* (2013.01); *A61F 2/90* (2013.01); *A61F 2/915* (2013.01); *A61F 2/95* (2013.01);
(Continued)

(58) Field of Classification Search
CPC ..................................... A61F 2/06; A61F 2/82
(Continued)

(56) References Cited

U.S. PATENT DOCUMENTS 5,480,431 A    1/1996   Freitag et al.
5,669,924 A    9/1997   Shaknovich
(Continued)

FOREIGN PATENT DOCUMENTS

EP    2085050    8/2009
WO    WO93/00869    1/1993
(Continued)

OTHER PUBLICATIONS

Extended European Search Report dated Apr. 10, 2015 for EP128413341.

(Continued)

*Primary Examiner* — Suzette J Gherbi
(74) *Attorney, Agent, or Firm* — Stoel Rives LLP

(57) ABSTRACT

An implantable device and method are disclosed for stenting an occlusion of an airway. The implantable device includes a cylindrical tube shaped proximal region, a flared distal region, and a non-bifurcated single lumen extending through the device. The proximal region defines a proximal portion of the lumen and the distal region defines a distal portion of the lumen. The distal region may flare outward laterally at a first angle and anteroposterior at a second angle, thereby forming an elliptically shaped distal opening to the lumen. The distal edge of distal opening may lie entirely in a plane orthogonal to a longitudinal axis of the device. Alternatively, the distal edge may be non-planar, such as concave or convex, when viewed in an anteroposterior direction. The implantable device may be formed of a scaffolding structure.

18 Claims, 12 Drawing Sheets

Related U.S. Application Data

(60) Provisional application No. 61/549,874, filed on Oct. 21, 2011.

(51) Int. Cl.
*A61F 2/915* (2013.01)
*A61F 2/90* (2013.01)
*A61F 2/95* (2013.01)

(52) U.S. Cl.
CPC .. *A61F 2002/043* (2013.01); *A61F 2230/0067* (2013.01); *A61F 2230/0069* (2013.01); *A61F 2250/0039* (2013.01)

(58) Field of Classification Search
USPC .............................................. 623/1.31, 23.65
See application file for complete search history.

(56) References Cited

U.S. PATENT DOCUMENTS

| | | | |
|---|---|---|---|
| 6,033,435 A | 3/2000 | Penn et al. | |
| 6,056,775 A | 5/2000 | Borghi et al. | |
| 6,099,560 A | 8/2000 | Penn et al. | |
| 6,514,281 B1 | 2/2003 | Blaeser et al. | |
| 6,645,242 B1 | 11/2003 | Quinn | |
| 6,666,884 B1 | 12/2003 | Webster | |
| 6,669,718 B2 | 12/2003 | Besselink | |
| 6,673,107 B1 | 1/2004 | Brandt et al. | |
| 6,709,440 B2 | 3/2004 | Callol et al. | |
| 6,746,476 B1 | 6/2004 | Hojeibane | |
| 6,761,733 B2 | 7/2004 | Chobatov et al. | |
| 6,770,091 B2 | 8/2004 | Richter et al. | |
| 6,802,859 B1 | 10/2004 | Pazienza et al. | |
| 6,821,295 B1* | 11/2004 | Farrar | A61F 2/06 623/1.31 |
| 6,953,475 B2 | 10/2005 | Shaolian et al. | |
| 7,736,387 B2 | 6/2010 | Pollock et al. | |
| 8,449,600 B2* | 5/2013 | Hartley | A61F 2/07 623/1.15 |
| 2001/0016767 A1 | 8/2001 | Wilson et al. | |
| 2001/0016768 A1 | 8/2001 | Wilson et al. | |
| 2001/0037138 A1 | 11/2001 | Wilson et al. | |
| 2002/0077692 A1 | 6/2002 | Besselink | |
| 2002/0183763 A1 | 12/2002 | Callol et al. | |
| 2003/0036793 A1 | 2/2003 | Richter et al. | |
| 2003/0139796 A1 | 7/2003 | Sequin et al. | |
| 2004/0148032 A1 | 7/2004 | Rutter et al. | |
| 2006/0106455 A1* | 5/2006 | Furst | A61F 2/82 623/1.31 |
| 2007/0021828 A1 | 1/2007 | Krolik et al. | |
| 2007/0055358 A1* | 3/2007 | Krolik | A61F 2/91 623/1.31 |
| 2008/0046065 A1* | 2/2008 | Hartley | A61F 2/07 623/1.13 |
| 2010/0076555 A1 | 3/2010 | Marten et al. | |
| 2011/0007954 A1 | 1/2011 | Suehling et al. | |
| 2013/0103163 A1* | 4/2013 | Krimsky | A61F 2/04 623/23.65 |
| 2014/0058433 A1* | 2/2014 | Barrett | A61B 17/12022 606/198 |
| 2014/0277560 A1* | 9/2014 | Walak | A61F 2/848 623/23.7 |
| 2014/0277561 A1* | 9/2014 | Jordan | A61M 27/002 623/23.7 |
| 2014/0316513 A1* | 10/2014 | Tang | A61F 2/2412 623/1.16 |
| 2015/0182668 A1* | 7/2015 | Ballard | D04H 1/42 623/1.13 |

FOREIGN PATENT DOCUMENTS

| | | |
|---|---|---|
| WO | WO/2009125899 | 10/2009 |
| WO | WO/2011072084 | 6/2011 |

OTHER PUBLICATIONS

International Search Report and Written Opinion dated Oct. 19, 2012 for PCT/US2012/061067.
Office Action dated Mar. 27, 2014 for U.S. Appl. No. 13/656,061.
International Search Report and Written Opinion dated Mar. 29, 2013 for PCT/US2012/061067.
Office Action dated Aug. 25, 2014 for U.S. Appl. No. 13/656,061.

\* cited by examiner

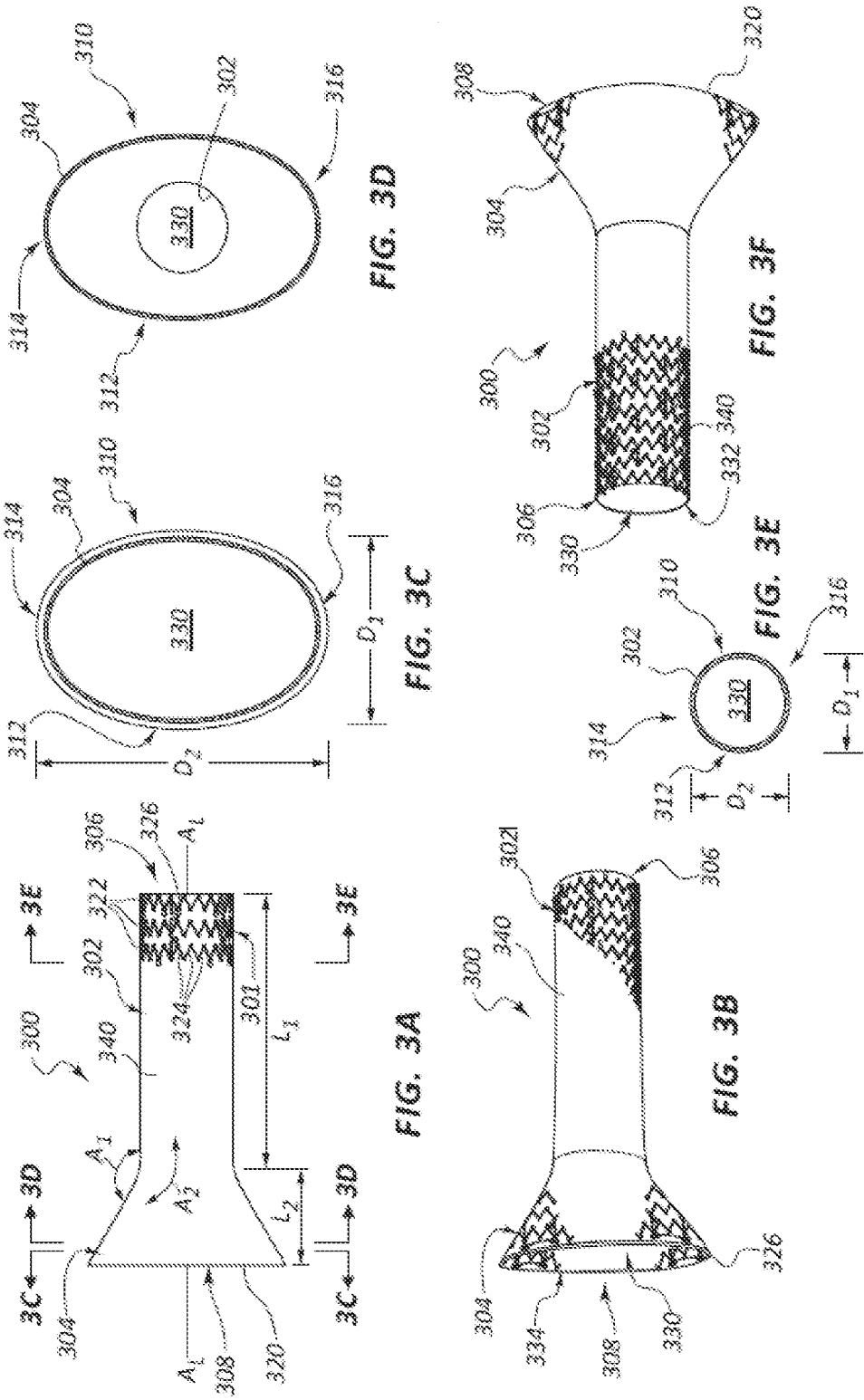

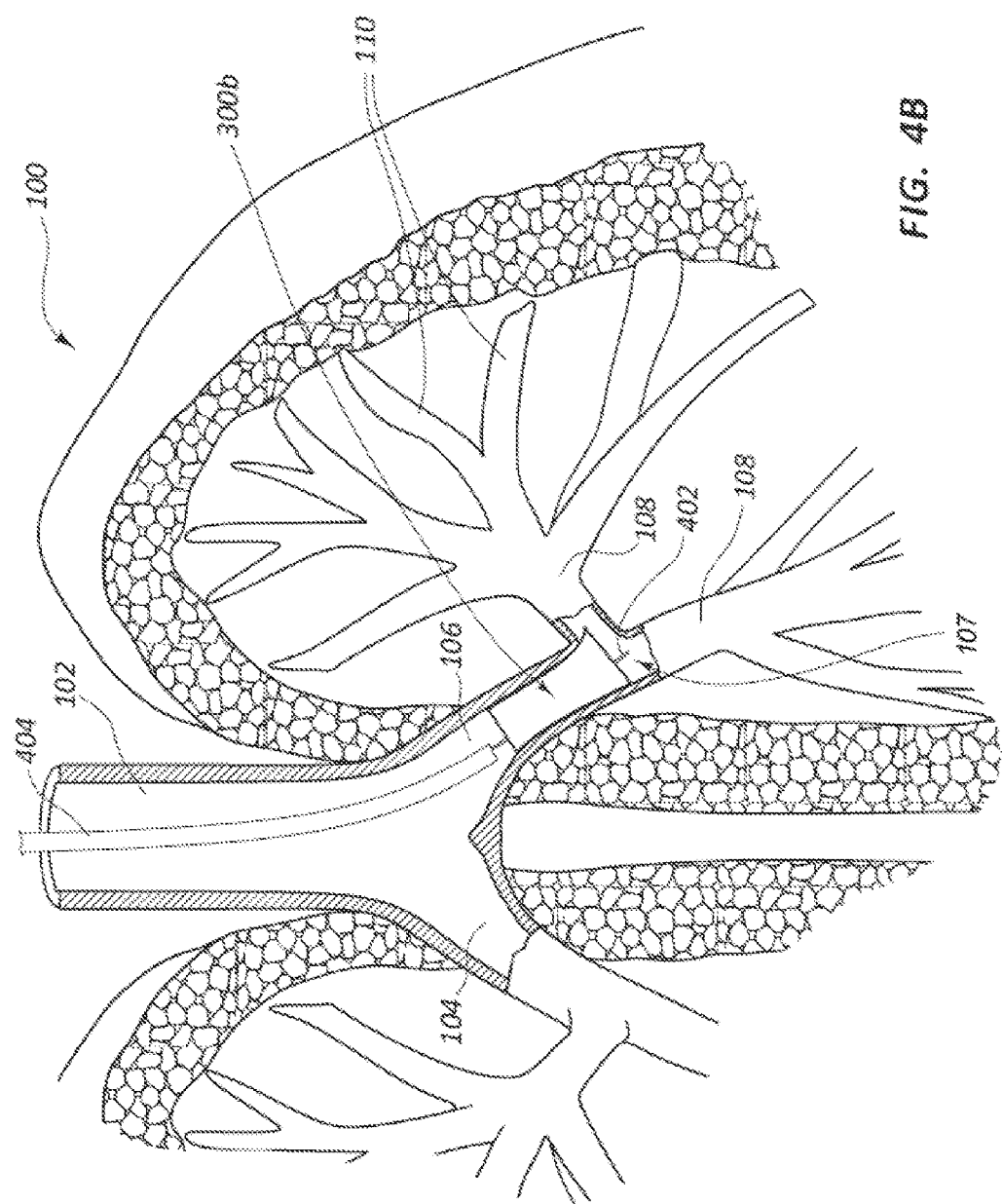

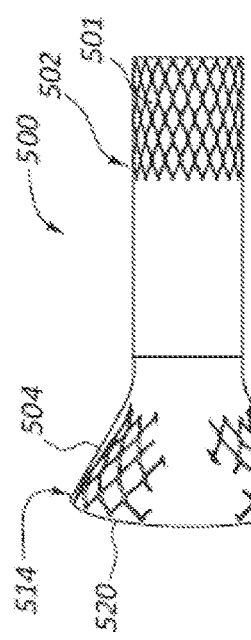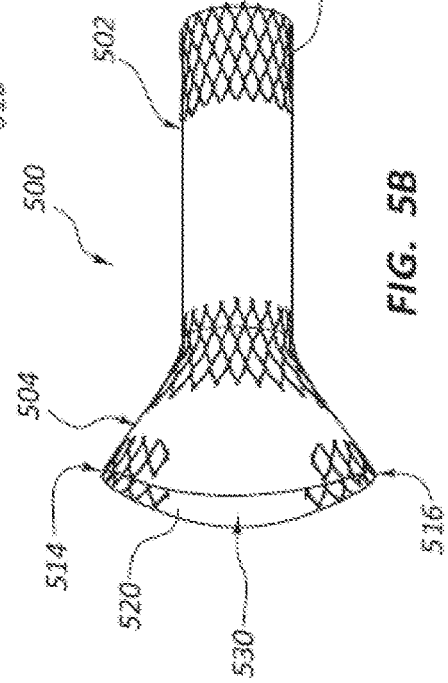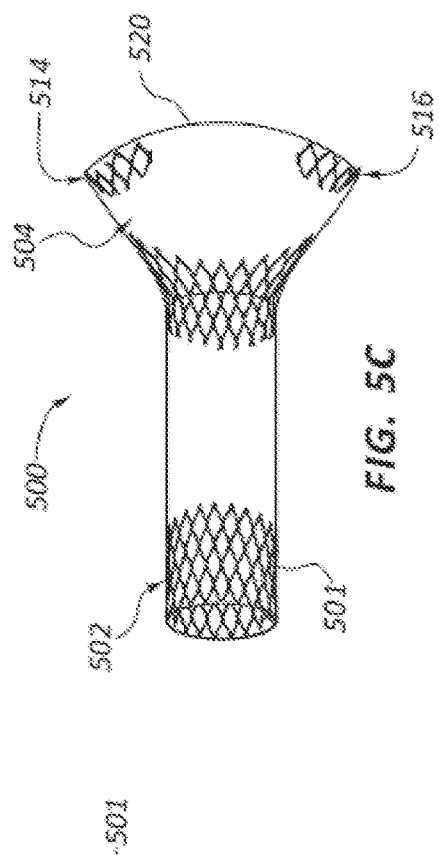

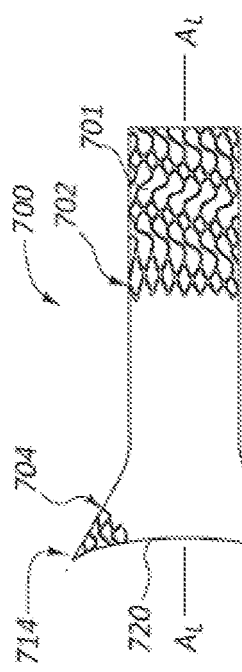
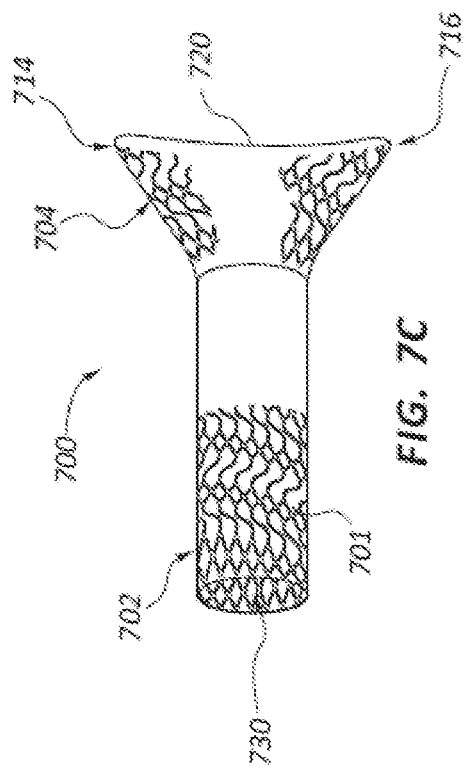
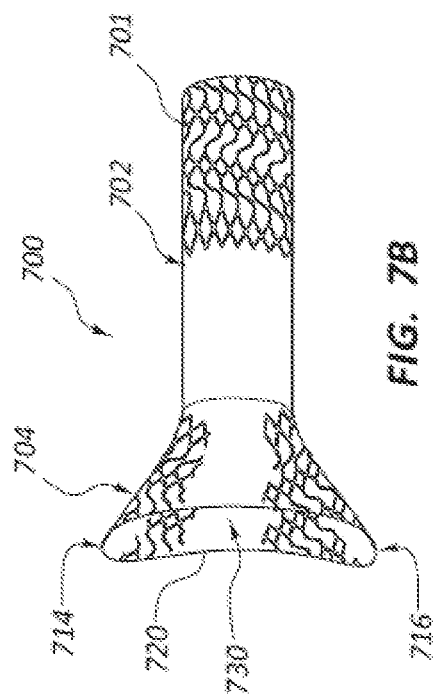

US 9,539,083 B2

DEVICES AND METHODS FOR STENTING AN AIRWAY

CROSS-REFERENCE TO RELATED APPLICATIONS

This application is a divisional application of U.S. patent application Ser. No. 13/656,061, entitled "CARINAL STENT," filed Oct. 19, 2012, which claims the benefit under 35 U.S.C. §119(e) of U.S. Provisional Patent Application No. 61/549,874, entitled "CARINAL STENT," filed Oct. 21, 2011, both of which are hereby incorporated by reference in their entireties.

TECHNICAL FIELD

The present disclosure relates generally to devices configured to be implanted within a body lumen. More particularly, the present disclosure relates to stents or similar prosthetic devices which, in certain embodiments, are configured to be disposed within an airway lumen, specifically, at a bifurcation of the airway lumen.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 3A is a side elevation view of an airway stent, according to one embodiment of the present disclosure that may be positioned at the main bifurcation junction of the airway, at or near the carinal region of the trachea.

FIG. 3B is a perspective view of the airway stent of FIG. 3A.

FIG. 3C is a cross-sectional distal-facing view of the airway stent of FIG. 3A.

FIG. 3D is a cross-sectional proximal-facing view of the airway stent of FIG. 3A.

FIG. 3E is another cross-sectional proximal-facing view of the airway stent of FIG. 3A.

FIG. 3F is another perspective view of the airway stent of FIG. 3A.

FIG. 4B is a partial sectional view of the human lungs with an airway stent, according to one embodiment, positioned at a bifurcation junction of the left main bronchus.

FIG. 5A is a side elevation view of an airway stent, according to another embodiment of the present disclosure.

FIG. 5B is a perspective view of the airway stent of FIG. 5A.

FIG. 5C is another perspective view of the airway stent of FIG. 5A.

FIG. 7A is a side elevation view of an airway stent, according to another embodiment of the present disclosure.

FIG. 7B is a perspective view of the airway stent of FIG. 7A.

FIG. 7C is another perspective view of the airway stent of FIG. 7A.

DETAILED DESCRIPTION

Figure 1:
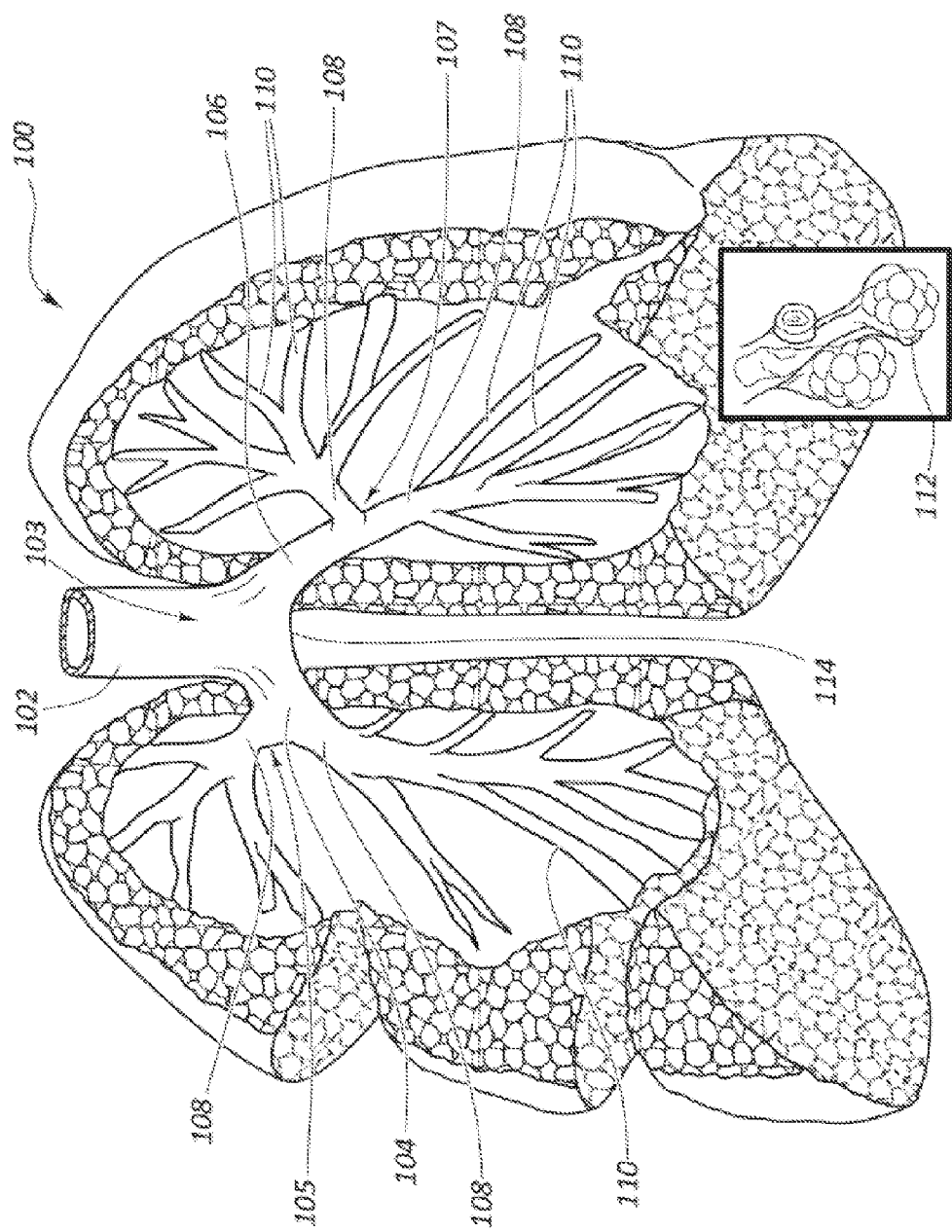
FIG. 1 is a diagram of the human lungs and principle parts of the airway.

Tracheo-bronchial (or "airway") stenting is more and more commonly performed to relieve difficult or labored breathing caused by a variety of conditions, including but not limited to extrinsic and/or intrinsic compression (e.g., stenosis), disease, and loss of cartilaginous support. Airway stenting can relieve airway obstruction caused by strictures, injury, disease, or the like that may not suitably be resolved by debridement, resection, reconstruction or the like. Airway stenting can also provide structural support for an airway structurally damaged through repairing an obstruction, such as by debridement, resection, or reconstruction.

In particular, stents are used in tumor patients, to ensure that the respiratory tract is kept open when the risk exists that the trachea may be compressed by a tumor. Stents are also used for stabilization of the airway in the context of tissue distension (malacia), or to seal off defects in the tracheal or bronchial walls (fistulae).

Because of the anatomic structure, airway stenting can be extremely difficult when an obstruction or structural failure of the airway involves the carinal region (the main bifurcation junction between the openings of the right and left principal bronchi) or another, more distal, bifurcation junction where the airway branches. The anatomy or structure of a bifurcation junction is not readily supported by a typical cylindrical stent. A bifurcation junction is not easily stented with a cylindrical stent because the cylindrical shape can result in partial occlusion of the branches. Similarly the branches create flaring or expansion of the airway, allowing instability in the positioning of the stent. A cylindrical stent can shift within the expanded area of the bifurcation junction and migrate down one of the branches, thereby partially or entirely occluding the other branch.

Though many of the examples provided herein refer to stents configured for use within the airway, the present disclosure is also applicable to a variety of stents designed for a variety of applications in various lumens of the body.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the implantable devices disclosed herein. As used herein, the proximal end of a medical device is the end nearest a practitioner during use, while the distal end is the opposite end. For example, the proximal end of a stent refers to the end nearest the practitioner when the stent is disposed within, or being deployed from, a deployment apparatus. For consistency throughout, these terms remain constant in the case of a deployed stent, regardless of the orientation of the stent within the body. In the case of an airway stent—deployed through the mouth of a patient—the proximal end will be nearer the head of the patient and the distal end nearer the abdomen (or deeper into the lungs) when the stent is in a deployed position.

Figure 2:
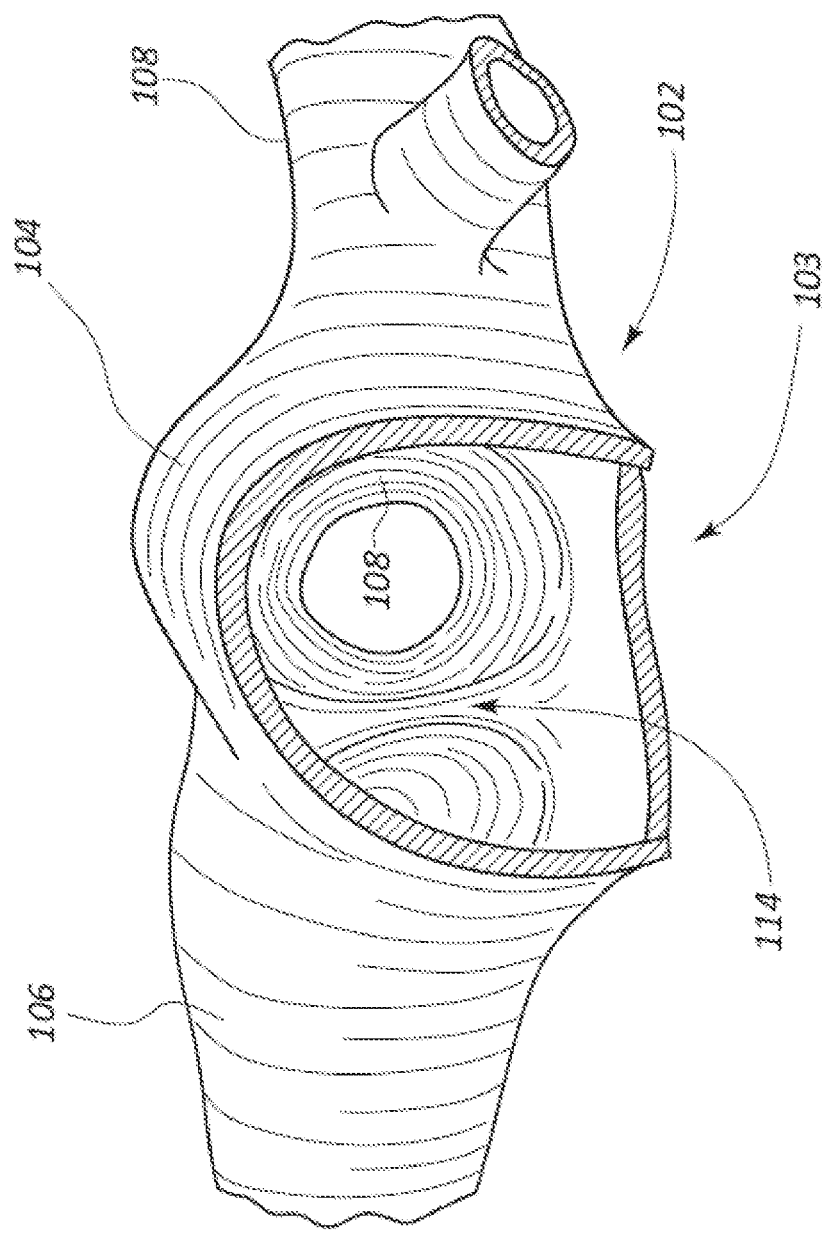
FIG. 2 is a cross-sectional view of the trachea looking distally to the carina and the right principal bronchus and the main left bronchus.

FIG. 1 is a diagram of the human lungs 100. The trachea 102 branches into the right principal bronchus 104 and the left principal bronchus 106. The bronchus 104, 106 in turn branch into bronchi 108, which in turn branch into bronchioles 110 and terminate at alveoli 112. The carina 114 of the trachea 102 is a cartilaginous ridge that runs anteroposteriorly at a first and main bifurcation junction 103 of the airway between the right principal bronchus 104 and the left principal bronchus 106. More distal (i.e., deeper into the lungs) bifurcation junctions, such as a bifurcation 105 of the right principal bronchus 104 (or right bronchus bifurcation junction 105) and the bifurcation 107 of the left principal bronchus 106 (or left bronchus bifurcation junction 107), may also include a cartilaginous ridge-like structure that is similar to the carina 114. FIG. 2 is a cross-sectional view of the main bifurcation junction 103, looking down the trachea 102 (i.e., distally, or deeper into the lungs) at the carina 114 and the right principal bronchus 104 and the left principal bronchus 106. The bronchi 108 of the right principal bronchus 104 are also illustrated.

Traditionally a Y-shaped stent has been used in bifurcation junctions of the airway. A Y-shaped stent can be inadequate because, among other things, it may not conform to the anatomy of the patient. For example, the angles of the branches of the stent may differ from the angles of the principal bronchi 104, 106 or other more distal airway branches. Also, the diameter of the branches of the stent may be smaller than the diameter of the respective airway branches. The greater the differences of the stent from the anatomy of the patient, the greater the chance for discomfort or even pain (e.g., the branches of the stent applying pressure to the sidewall of the bronchi or altering the positioning of the bronchi) and for partial or complete obstruction of the airway (e.g., a stent with a diameter that may be too small will unavoidably function as an obstruction of at least a portion of the airway and reduce airflow). The present disclosure provides novel systems and methods for stenting bifurcation junctions of the airway, including the main bifurcation junction 103, the bronchus bifurcation junctions 105, 107, and more distal bifurcation junctions such as bifurcation junctions of the bronchi 108 and/or bronchioles 110.

Embodiments may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

FIGS. 3A-3F are an airway stent 300 according to one embodiment of the present disclosure. FIG. 3A is a side elevation view of the airway stent 300, providing an anteroposterior view of the airway stent 300. FIG. 3B is a perspective view of the airway stent 300. FIG. 3C is a cross-sectional distal-facing view of the airway stent 300. FIG. 3D is a cross-sectional proximal-facing view of the airway stent 300. FIG. 3E is another cross-sectional proximal-facing view of the airway stent 300. FIG. 3F is another perspective view of the airway stent 300.

The airway stent 300 may be an implantable device configured for placement in a lumen of an airway to treat, for example, a stricture, closure, blockage or occlusion of the airway. The airway stent 300 may be configured to resist stricture and otherwise function to maintain patency of the airway. Additionally, the stent 300 may comprise a variety of components, and the parameters of these components (e.g., shape, length, thickness, position, etc.) may be configured to provide the stent 300 with certain properties. For example, the stent 300 may be configured to distribute transverse loads or to change shape in response to certain forces.

Referring collectively to FIGS. 3A-3F, the airway stent 300 may be formed of a suitable material configured in a scaffolding structure 301 (only partially depicted for simplicity) or mesh and formed into a tube having a substantially cylindrical shape (although one or more cross-sectional diameters of the tube may vary independently as will be described below). The scaffolding structure 301 may be constructed of a memory material, such as Nitinol®, including ASTM F2063.

The thickness of the scaffolding structure 301 may be between about 0.30 mm and about 0.60 mm. In other embodiments, the thickness of the scaffolding structure 301 may be between about 0.35 mm and about 0.55 mm. In other embodiments, the thickness of the scaffolding structure 301 may be between about 0.40 mm and about 0.50 mm. In other embodiments, the thickness of the scaffolding structure 301 may be about 0.45 mm.

As illustrated best in FIG. 3A, the scaffolding structure 301 may be formed of multiple annular segments 322 (or rings) disposed on a circumference and defining at least a portion of the generally cylindrical shape of the scaffolding structure 301. Each annular segment 322 may comprise a plurality of interconnected strut arms 324. For example, the strut arms 324 may be connected such that they form a zigzag pattern, defining alternating "peaks" and "valleys," around the annular segment 322. (As used herein, "peaks" refer to the relative high points and "valleys" refer to the relative low points where strut arms 324 arranged in a zigzag pattern connect. In other words, the peaks and valleys may be relative to one end 306, 308 of the stent 300, rather than relative to the circumference of the stent 300.) In some embodiments adjacent strut arms 324 may form acute angles relative to each other.

The adjacent annular segments 322 may be arranged in rows around a longitudinal axis $A_L$ of the generally cylindrical shape of the scaffolding structure 301. The rows may be arranged in the longitudinal direction of the generally cylindrical shape of the scaffolding structure 301. Adjacent annular segments 322 may be coupled to each other by connectors 326.

The components and elements of the scaffolding structure 301, including the annular segments 322, the strut arms 324, and the connectors 326, may be configured to balance transverse forces applied to the scaffolding structure 301, for example, to reduce the incidence of infolding. The components and elements of the scaffolding structure 301 may be configured to allow at least a portion of the scaffolding structure 301 to decrease in diameter in response to an axial force applied to the scaffolding structure 301, for example to enable sheathing of the stent 300 in a deployment device and/or retrieval of the stent 300.

Some example embodiments of a scaffolding structure 301 are disclosed in U.S. patent application Ser. No. 10/288,615 (issued as U.S. Pat. No. 7,527,644) and U.S. patent application Ser. No. 13/285,358, which are hereby incorporated herein by reference in their entirety.

In the figures, only portions of the scaffolding structure 301 are shown, for simplicity. As will be appreciated, the entire stent 300 may be defined by an integrally formed scaffolding structure 301. In other embodiments, the scaffolding structure 301 may form merely a portion of the stent 300, such as all or a portion of a proximal region 302 (or a mid-body) and/or all or a portion of a distal region 304 (or a flared region), and other portions of the stent 300 may be formed by another structure and/or material, such a woven Nitinol wire mesh that may be coupled to the laser cut scaffolding structure 301 through a winding or weaving process.

The scaffolding structure 301 may be coated, or otherwise be enclosed in a cover 340 formed of a flexible material. The cover 340 may be elastomeric, polymeric, or comprised of any other material known in the art. In some embodiments, the cover 340 may include polyurethane, while in certain embodiments the cover may be comprised only of polyurethane. In some embodiments, the cover 340 may include silicone, while in certain embodiments the cover may be comprised only of silicone. In some embodiments, an internal surface of the cover may be coated with a hydrophilic layer. Some example embodiments of coverings are disclosed in U.S. patent application Ser. No. 10/669,450 (issued as U.S. Pat. No. 7,637,942), U.S. patent application Ser. No. 10/718,217 (issued as U.S. Pat. No. 7,959,671), and U.S. patent application Ser. No. 12/616,455 (issued as U.S. Pat. No. 8,206,436), all of which are hereby incorporated herein by reference in their entirety.

The airway stent 300 may comprise a proximal region 302 (or a mid-body) and a distal region 304 (or a flared region). The distal region 304 may be at a distal end 308 of the proximal region 302. A non-bifurcated single lumen 330 extends axially through the stent 300 along a longitudinal axis $A_L$ of the stent 300. The airway stent 300 is configured such that a proximal end 306 of the proximal region 302 can be positioned in a portion of the airway and a distal end 308, including the distal region 304, can be positioned in a bifurcation junction of the airway. For example, the proximal end 306 may be positioned in the trachea 102 (FIG. 1) and the distal region 304 can be positioned in the main bifurcation junction 103 (FIGS. 1 and 2) at the carinal region, as shown, for example in FIG. 4. The airway stent 300 may have an anterior side 310, a posterior side 312, a left side 314, and a right side 316 (see FIG. 3C). In some embodiments, the airway stent 300 may have a specific orientation when disposed in the airway. In other words, the airway stent 300 may only fit in the target bifurcation junction oriented a certain way.

The proximal region 302 may have a hollow substantially cylindrical shape. Particularly at or near the proximal end 306, the shape of the proximal region 302 may be substantially cylindrical. The proximal region 302 may be hollow to define a portion of a lumen 330 through the stent 300. The lumen 330 may extend axially along a longitudinal axis $A_L$ of both the cylindrical shape of the proximal region 302 and the stent 300 from a first opening 332 at the proximal end 306 of the stent 300 to a second opening 334 at the distal end 308 of the stent 300. A cross-section of the proximal region 302 may be substantially circular, particularly at the proximal end 306. The circular cross-section of the proximal region 302 is shown in FIG. 3D. The first opening 332 may be circular. A transverse cross-section of the proximal region 302 and the lumen 330 at a distal end of the proximal region 302 may be circular or approximately circular. Described differently, a diameter D1 of the proximal region 302 extending from the anterior side 310 to the posterior side 312 (an anteroposterior diameter) may be substantially the same as a diameter D2 of the proximal region 302 extending from the left side 314 to the right side 316 (a lateral diameter). For example, in one embodiment, the airway stent 300 may be designed and configured for placement in the trachea 102 (see FIG. 1) and may have a cross-sectional diameter D1, D2 of the proximal region 302 that is between approximately fourteen millimeters and twenty-two millimeters. In another embodiment, the airway stent 300 may be designed and configured for placement in a bronchial portion of the airway (e.g., in the bronchi 108 shown in FIG. 1). An airway stent 300 configured for placement in the left main bronchus 106, the cross-sectional diameter D1, D2 of the proximal region 302 may between approximately six millimeters and sixteen millimeters. As can be appreciated, in an airway stent 300 configured for placement in the bronchioles, the diameter D1, D2 of the proximal region 302 may be smaller.

In other embodiments, the cross-sectional shape of the proximal region 302 and/or the lumen 330 may vary along the length L1 of the stent 300, for example to conform to the shape and/or features of the airway.

The length L1 of the proximal region 302 can vary as appropriate to provide desired stenting support and/or to conform to patient anatomy. For example, an airway stent 300 configured for placement in the trachea 102, to stent the main bifurcation junction 103 (see FIGS. 1 and 2), may have a proximal region 302 with a length L1 that is between approximately thirty millimeters and ninety millimeters. An airway stent 300 configured for placement in a bronchial portion of the airway (e.g., in the bronchi 108 of FIGS. 1 and 2) may have a proximal region 302 with a length L1 that is between approximately fifteen millimeters and fifty millimeters. As can be appreciated, in an airway stent 300 configured for placement in the bronchioles, the length L1 of the proximal region 302 may be smaller.

The distal region 304 is positioned at the distal end 308 of the stent 300 and/or the proximal region 302. A proximal end of the distal region 304 couples to and conforms to a circumference of a distal end of the proximal region 302. The distal region 304 may be configured to flare distally and outwardly to substantially conform to the anatomy of a bifurcation junction. The distal region 304 may define a distal portion of the lumen 330 through the stent 300 and a second opening 334 into the lumen 330. An airway bifurcation junction, such as the main bifurcation junction 103 near the carinal region, naturally flares. However, the anteroposterior diameter of the airway in a bifurcation junction may not flare to the same degree as the lateral diameter of the airway. The lateral diameter may typically flare to a greater degree than the anteroposterior diameter. Accordingly, a cross-section of the distal region 304 of the stent 300 may have a substantially elliptical shape, having a greater lateral diameter D2 than an anteroposterior diameter D1, as shown in FIGS. 3C and 3E. (The anteroposterior diameter D1 and the lateral diameter D2 may be transverse to and may intersect the longitudinal axis $A_L$ of the stent 300 and may also be referred to herein as first and second diameters, respectively.) For example, an airway stent 300 configured for placement in the trachea 102, to stent the main bifurcation junction 103 (see FIGS. 1 and 2), may have a distal region 304 with an anteroposterior diameter D1 at the edge 320 of the distal region 304 that is between approximately fourteen millimeters and twenty-two millimeters and a lateral diameter D2 at the edge 320 of the distal region 304 that is between approximately nineteen millimeters and thirty-two millimeters. An airway stent 300 configured for placement in a bronchial portion of the airway (e.g., in the bronchi 108) may have a distal region 304 with an anteroposterior diameter D1 at the edge 320 of the distal region 304 that is between approximately six millimeters and sixteen millimeters and a lateral diameter D2 that is between approximately twelve millimeters and twenty-eight millimeters. As can be appreciated, in an airway stent 300 configured for placement in the bronchioles, the diameter D1, D2 of the distal region 302 may be smaller.

The degree or angle at which the anteroposterior diameter D1 and the lateral diameter D2 may flare can vary. Differing degrees of flaring are possible, and can be configured independently as desired according to the anatomy of a patient. Stated differently, an angle A1 at which the distal region 304 flares anteroposteriorly can vary independently from the angle A2 at which the distal region 304 flares laterally.

A length L2 of the distal region 304 can vary, for example, to provide desired stenting support and according to patient anatomy. As an example, an airway stent 300 configured for placement in the trachea 102, to stent the main bifurcation junction 103 (see FIGS. 1 and 2), may have a distal region 304 with a length L2 that is between approximately five millimeters and fifteen millimeters. An airway stent 300 configured for placement in a bronchial portion of the airway (e.g., in the bronchi 108) may have a distal region 304 with a length L2 that is between approximately two millimeters and ten millimeters. As can be appreciated, in an airway stent 300 configured for placement in the bronchioles, the length L2 of the distal region 304 may be smaller.

In the FIGS. 3A, 3B, and 3F, the airway stent 300 is depicted as having an abrupt transition from the proximal region 302 to the distal region 304. However, as can be appreciated, in other embodiments the transition from the proximal region 302 to the distal region 304 may be gradual. In some embodiments, the transition may be imperceptible. The proximal region 302 may simply gradually flare distally. Moreover, the transition from a circular cross-section of the proximal region 302 to an elliptical cross-section of the distal region 304 may be gradual and nearly imperceptible.

In the illustrated embodiment of FIGS. 3A-3F, the distal edge 320 of the distal region 304 may be configured to have a planar configuration, meaning that the distal edge 320 may appear substantially flush or planar (for example, relative to a plane orthogonal to the longitudinal axis of the stent) when viewing the stent 300 from the side, such as anteroposteriorly or laterally. As appreciated, other configurations are possible, as will be described below with reference to FIGS. 5A-5C and 7A-7C.

The flare of the distal region 304 and/or the elliptical shape of the distal edge 320 may serve as anti-migration features to secure the stent 300 from proximal (toward the mouth) and/or distal migration (down deeper into the airway). The stent 300, and in particular the scaffolding structure 301, may include additional anti-migration features. For example, one or more strut arms 324 may be slightly raised above (outward from) an outer circumference of the scaffolding structure 301.

Figure 4A:
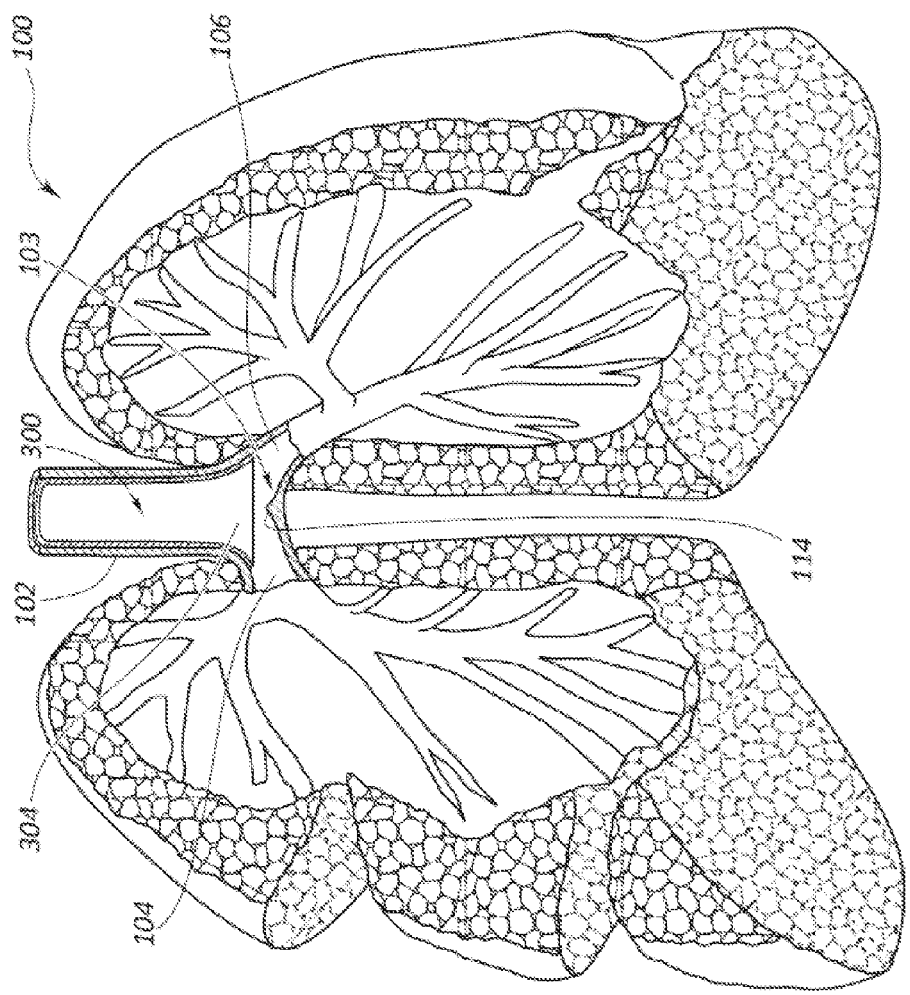
FIG. 4A is a partial sectional view of the human lungs with the airway stent of FIGS. 3A-3F positioned at the main bifurcation junction.

FIG. 4 is a cross-sectional view of the human lungs 100 and a sectional view of the airway stent 300 of FIGS. 3A-3F positioned in the airway to stent the trachea 102 near the carinal region and/or the main bifurcation junction 103. The main body 302 of the stent 300 is disposed within the trachea 102 and the distal region 304 flares and opens into the main bifurcation junction 103. The distal region 304 is disposed in the main bifurcation junction 103 above (proximal to) the carina 114 and between the right bronchus 104 and the left bronchus 106.

Presently available airway stents are delivered or deployed using a rigid bronchoscope. The rigidity, size, shape, and/or configuration of a bronchoscope prevent deployment of presently available airway stents deeper than the main bifurcation junction (or the tracheal bifurcation junction) at the carina 114. Moreover, presently available stents for stenting a bifurcation junction are Y-shaped (with a bifurcated lumen) and must be deployed by a rigid bronchoscope, and thus cannot be deployed distal to the carina 114 and/or the bronchi 104, 106. By contrast, the disclosed embodiments may be configured to be deployed with a deployment mechanism that can be guided over a guide wire. Accordingly, the embodiments of the present disclosure can be deployed almost anywhere a guide wire can be positioned within the lungs, including bifurcation junctions of the main bronchi 104, 106 and/or bifurcation junctions distal to the main bronchi 104, 106.

FIG. 4B is a sectional view of the human lungs 100 with an airway stent 300b positioned at left bronchus bifurcation junction 107 at a distal end of the left main bronchus 106. In FIG. 4B, guide wire 402 is shown, which may be used in positioning and/or guiding a tubular member 404 of a deployment apparatus into the airway to a desired target location. The tubular member 404 is illustrated in FIG. 4B advanced down the trachea 102 over a portion of the guide wire 402. A flared portion of the stent 300b is positioned in the bifurcation junction where the left main bronchus 106 branches into secondary bronchi 108. The stent 300b is positioned proximal to the bronchioles 110.

Figure 4C:
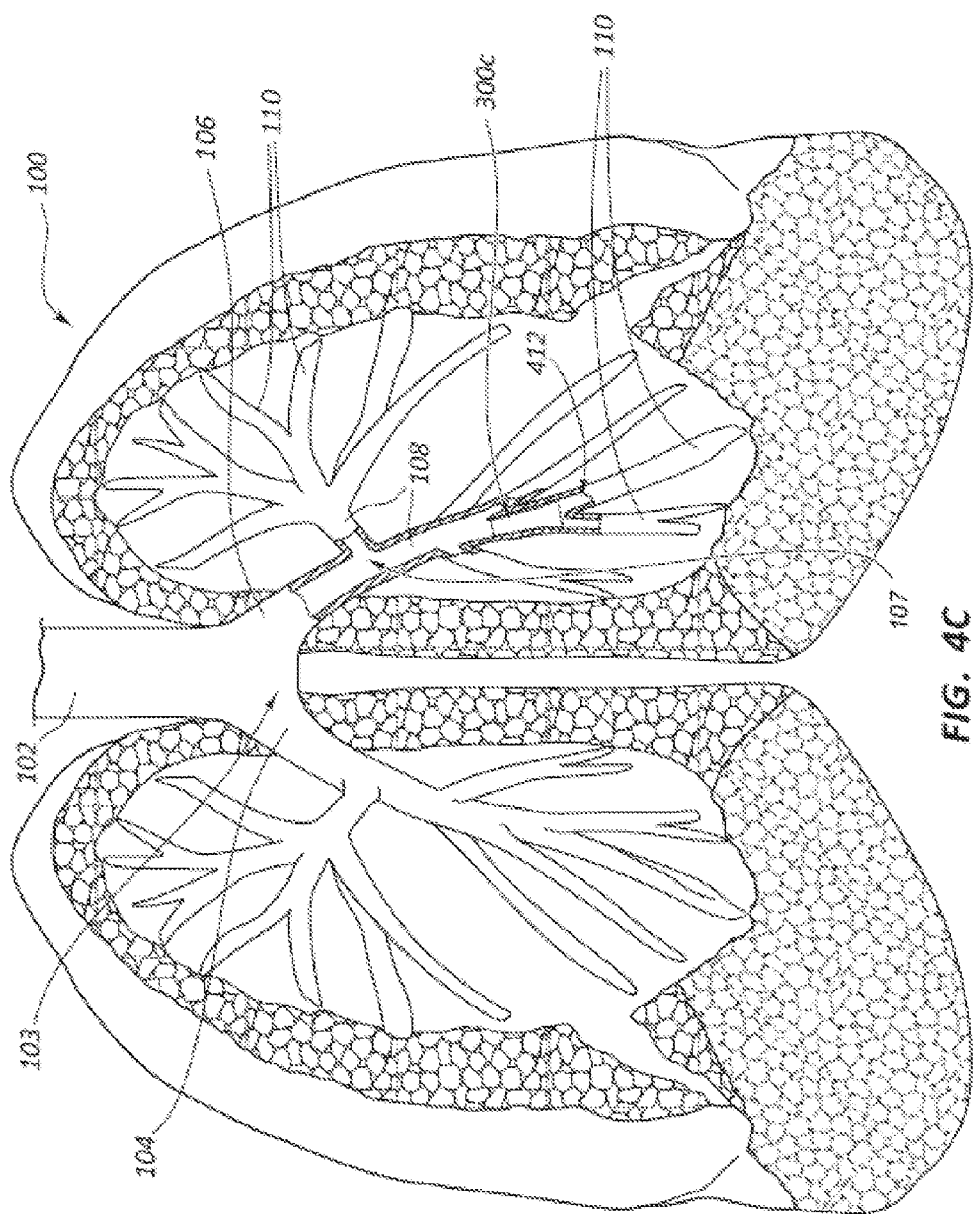
FIG. 4C is a partial sectional view of the human lungs with an airway stent, according to one embodiment, positioned in the airway at a position distal to the left main bronchus.

FIG. 4C is a sectional view of the human lungs 100 with an airway stent 300c positioned at a location distal to the left main bronchus 106. More specifically, the airway stent 300c is deployed within a branch of the airway at a bifurcation junction 412 that is distal to the left bronchus bifurcation junction 107 located at a distal end of the left principal bronchus 106 of the airway. The airway stent 300c may be deployed within bronchi 108 and/or bronchioles 110 that branch into bronchioles 110. As noted above, the embodiments of the present disclosure can be deployed almost anywhere a guide wire can be positioned within the lungs, including bifurcation junctions relatively deep within the airway and far distal to the main bronchi 104, 106 and the main bifurcation junction 103.

FIGS. 5A-5C illustrate an airway stent 500, according to another embodiment of the present disclosure. The airway stent 500 may include a distal region 504 with a convex configuration, meaning that the distal edge 520 of the distal region 504 may appear convex when viewed anteroposteriorly from the side. FIG. 5A is a side elevation view of the airway stent 500 viewed anteroposteriorly. FIG. 5B is a perspective view of the airway stent 500 of FIG. 5A. FIG. 5C is another perspective view of the airway stent 500 of FIG. 5A.

The stent 500 of FIGS. 5A-5C may resemble the stent 300 described above with respect to FIGS. 3A-3F. Accordingly, like features may be designated with like reference numerals, with the leading digits incremented to "5." Relevant disclosure set forth above regarding similarly identified features thus may not be repeated hereafter. Moreover, specific features of the stent 500 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent 500. Any suitable combination of the features and variations of the same described with respect to the stent 300 can be employed with the stent 500, and vice versa. This pattern of disclosure applies equally to further embodiments depicted in subsequent figures and described hereafter.

Referring collectively to FIGS. 5A-5C, the airway stent 500 includes a proximal region 502 (or a mid-body) and a distal region 504 (or a flared region). A non-bifurcated single lumen 530 may be defined through the airway stent 500. The airway stent 500 may be formed of a suitable material configured in a scaffolding structure 501 (only partially depicted for simplicity). The scaffolding structure 501 may form or define at least a portion of the mid body 502 and/or the distal region 504. The scaffolding structure 501 may form a hollow, substantially cylindrical shaped tube (although one or more cross-sectional diameters of the tube may vary independently as will be described below). The scaffolding structure 501 may be constructed of a memory material, such as Nitinol®, including ASTM F2063.

As illustrated in FIGS. 5A-5C, the scaffolding structure 501 may be formed of multiple annular segments, similar to the annular segments 322 of the stent 300 shown in FIGS. 3A-3F and described above with respect to the same. However, the scaffolding structure 501 may include annular segments that may be interconnected to one or more adjacent annular segments by a plurality of connectors, or otherwise directly interconnect, to form diamond-shaped cells.

As mentioned above, the distal region 504 of the airway stent 500 may have a convex configuration. The airway stent 500 having the distal region 504 in a convex configuration may be positioned in a bifurcation junction of an airway differently than an airway stent having a planar configuration, such as the stent 300 of FIGS. 3A-3F and 4. In particular, than the left side 514 and right side 516 of the distal edge 520 of airway stent 500 may sit more proximal (or higher, with less depth) in the airway than the corresponding left side 314 and right side 316 of the distal edge 320 of airway stent 300, which has a planar configuration.

The left side 514 and right side 516 of the distal region 504 of the airway stent 500 may form and/or comprise lateral support regions. The depth of these lateral support regions within the airway may be dependent on the concavity or convexity of the distal region 504. When a tumor is positioned substantially down a branch of a bifurcation junction, for example on a wall opposite the carina 114 (or analogous ridge-like structure of another bifurcation junction), positioning the lateral support regions more distal may be desirable. In other words, an airway stent having a planar configuration, such as the airway stent 300 of FIGS. 3A-3F and 4, or an airway stent having a convex configuration, such as the airway stent 700 of FIGS. 7A-7C and 8, which is described more fully below, may better perform a desired stenting function or treatment.

By contrast, the anatomy of a patient may be such that the branches of a target bifurcation junction (i.e., the bifurcation junction to be stented) may branch at a relatively high angle. As a result, the branches may be partially occluded by lateral support regions positioned too deeply in the target bifurcation junction. Accordingly, a convex configuration may be desirable to maintain or preserve patency of the airway.

Figure 6:
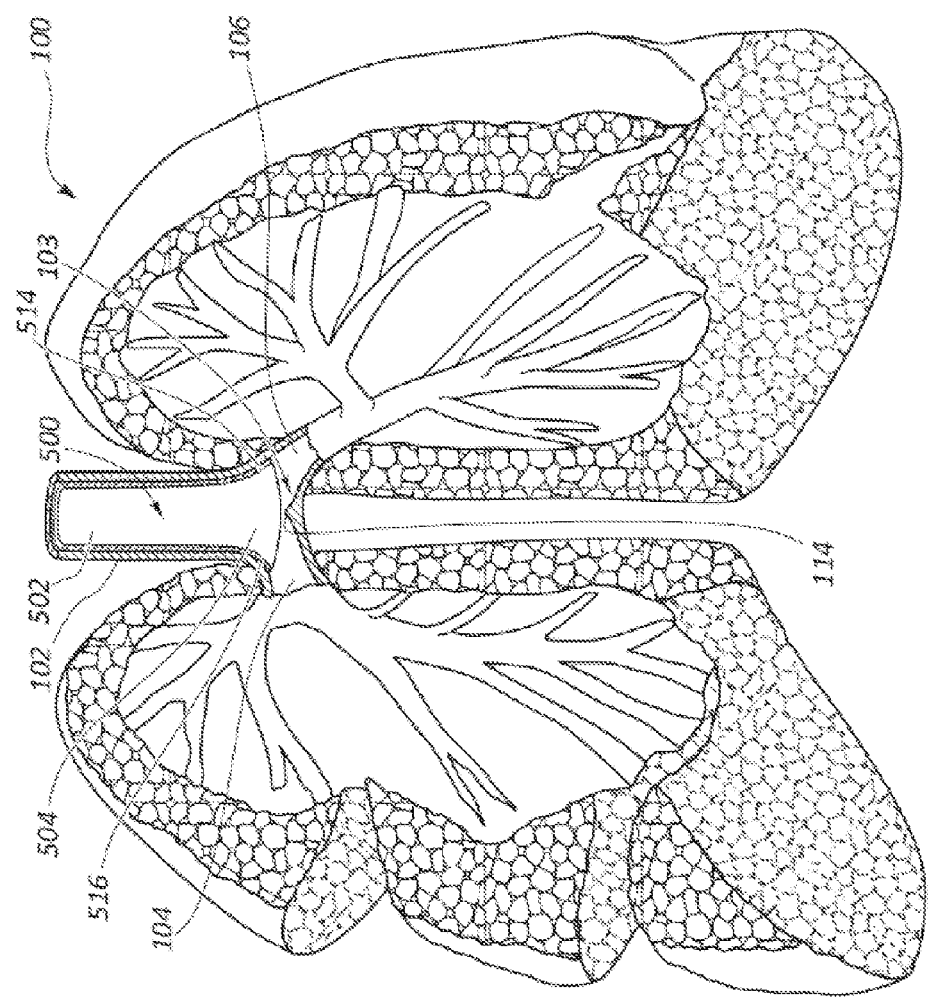
FIG. 6 is a partial sectional view of the airway stent of FIGS. 5A-5C positioned in an airway at the main bifurcation junction.

FIG. 6 is a partial sectional view of the airway stent of FIGS. 5A-5C positioned in an airway to stent the trachea 102 at or near the carinal region and/or the main bifurcation junction 103. The main body 502 of the stent 500 is disposed within the trachea 102 and the distal region 504 flares and opens into the main bifurcation junction 103. As illustrated in FIG. 6, the left and right sides 514, 516, or lateral support regions, of the distal region 504 are positioned high against an upper surface of the main bifurcation junction 103, thereby avoiding occlusion of the right and left bronchi 104, 106. The distal region 504 is disposed in the main bifurcation junction 103 above (proximal to) the carina 114 and between the right bronchus 104 and the left bronchus 106.

As can be appreciated, a variety of configurations of the distal region are possible to provide varying lateral support while avoiding unnecessary occlusion of the branches of a bifurcation junction of an airway.

FIGS. 7A-7C illustrate an airway stent 700, according to another embodiment of the present disclosure. The airway stent 700 may include a distal region 704 with a concave configuration, meaning that the distal edge 720 of the distal region 704 may appear convex when viewed anteroposteriorly from the side. FIG. 7A is a side elevation view of the airway stent 700. FIG. 7B is a perspective view of the airway stent of FIG. 7A. FIG. 7C is another perspective view of the airway stent of FIG. 7A.

The stent 700 of FIGS. 7A-7C may resemble the stent embodiments described above. Accordingly, like features may be designated with like reference numerals, with the leading digits incremented to "7." Relevant disclosure set forth above regarding similarly identified features thus may not be repeated hereafter. Moreover, specific features of the stent 700 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent 700. Any suitable combination of the features and variations of the same described with respect to the previously disclosed stents can be employed with the stent 700, and vice versa. This pattern of disclosure applies equally to further embodiments depicted in subsequent figures and described hereafter.

Referring collectively to FIGS. 7A-7C, the airway stent 700 includes a proximal region 702 (or a mid-body) and a distal region 704 (or a flared region). A non-bifurcated single lumen 730 may be defined through the airway stent 700. The airway stent 700 may be formed of a suitable material configured in a scaffolding structure 701 (only partially depicted for simplicity). The scaffolding structure 701 may form or define at least a portion of the mid body 702 and/or the distal region 704. The scaffolding structure 701 may form a hollow, substantially cylindrical shaped tube (although one or more cross-sectional diameters of the tube may vary independently as will be described below). The scaffolding structure 701 may be constructed of a memory material, such as Nitinol®, including ASTM F2063.

As illustrated in FIGS. 7A-7C, the scaffolding structure 701 may be formed of multiple annular segments, similar to the annular segments 322 of the stent 300 shown in FIGS. 3A-3F and described above with respect to the same. However, the scaffolding structure 701 may include annular segments that may be configured to interconnect to one or more adjacent annular segments by a plurality of connectors, or otherwise directly interconnect in a helical pattern.

The scaffolding structure 701 may comprise one or more rows of strut arms (e.g., annular segments) arranged and interconnected in a series of turns to form a helix or helical pattern that wraps or winds around the longitudinal axis $A_L$ of the stent 700. The helical pattern of strut arms may be disposed on a circumference and may define at least a portion of the generally cylindrical shape of the scaffolding structure 301. As can be appreciated, in some embodiments, the entire length of the stent 300 may comprise a helical pattern of interconnected strut arms. In other embodiments, however, only a portion of the stent 700, for example, a proximal zone or a transition zone, may comprise a helical pattern. The helical pattern may be right-handed or left-handed depending on which direction the one or more rows of strut arms wrap around the longitudinal axis $A_L$.

The helical pattern may comprise a row of strut arms arranged to form a zigzag pattern, defining alternating "peaks" and "valleys," that may wrap around the longitudinal axis $A_L$ of the stent 700. In some embodiments, the "peaks" and "valleys" on a row of strut arms may be coupled by connectors. In particular, the "peaks" on one turn of the helical pattern may be coupled to the "valleys" on an adjacent turn of the helical pattern via connectors. As used herein, a "turn" of the helical pattern refers to a segment of strut arms that wraps 360 degrees around the longitudinal axis $A_L$ of the stent 700. Adjacent turns of the helical pattern may adjoin each other at an end.

The helical pattern may wrap around the longitudinal axis $A_L$ of the stent 700 at an angle. The angle may vary and may affect the structural properties of the stent 700. In some embodiments, the angle may remain substantially constant throughout the helical pattern. In other embodiments, however, the angle may vary throughout the helical pattern.

As mentioned above, the distal region 704 of the airway stent 700 may have a concave configuration. The airway stent 700 having the distal region 704 in a concave configuration may be positioned in a bifurcation junction of an airway differently than an airway stent having a planar configuration, such as the stent 300 of FIGS. 3A-3F and 4, and differently than an airway stent having a convex configuration, such as the stent 500 of FIGS. 5A-5C and 6. In particular, the lateral sides (e.g., the left side 714 and right side 716) of the distal edge 720 of the airway stent 700 may sit more distal in the airway than the corresponding lateral sides (e.g., left side 314, 514 and right side 316, 516) of the distal edge 720 of the airway stent 700.

The left side 714 and right side 716 of the distal region 704 of the airway stent 500 may form and/or comprise lateral support regions. The depth of these lateral support regions within the airway may be dependent on the concavity or convexity of the distal edge of the distal region 704. When a tumor or other occlusion is positioned substantially down a branch of a bifurcation junction, for example on a wall opposite the carina 114 (or an analogous ridge-like structure of another target bifurcation junction), positioning the lateral support regions more distal may be desired. An airway stent having a concave configuration may better perform a desired stenting function or treatment on more distal occlusions.

Figure 8:
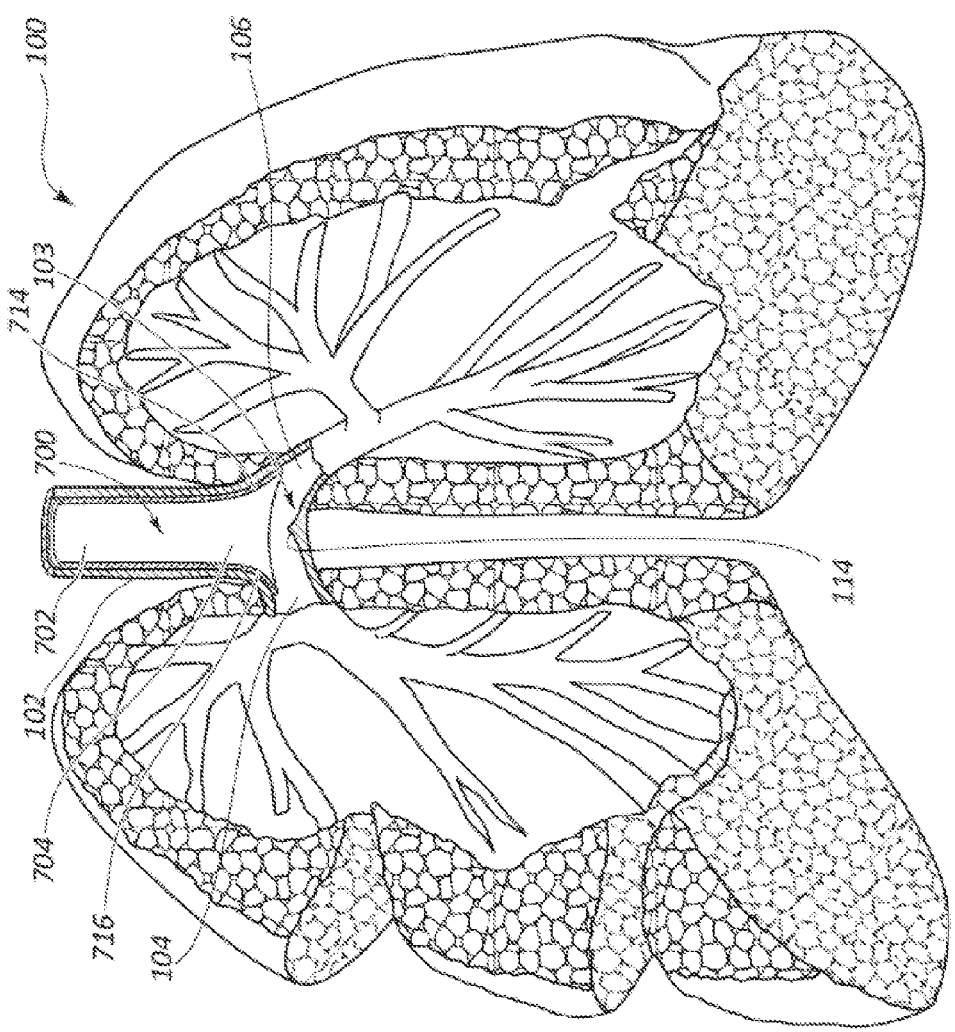
FIG. 8 is a partial sectional view of the airway stent of FIGS. 7A-7C positioned in an airway at the main bifurcation junction.

FIG. 8 is a partial sectional view of the airway stent of FIGS. 7A-7C positioned in an airway to stent the trachea 102 at or near the carinal region and/or the main bifurcation junction 103. The main body 702 of the stent 700 is disposed within the trachea 102. The distal region 704 is disposed in the main bifurcation junction 103 above (proximal to) the carina 114 and between the right bronchus 104 and the left bronchus 106. The distal region 704 flares and opens into the main bifurcation junction 103. As illustrated in FIG. 8, the left and right sides 714, 716, or lateral support regions, of the distal region 704 are positioned to extend deeper into the airway against an upper surface of the main bifurcation junction 103, thereby providing stenting support at a greater depth into the right and left bronchi 104, 106.

As can be appreciated, a variety of configurations of the distal region 704 are possible to provide varying lateral support while avoiding unnecessary occlusion of the branches of a bifurcation junction of an airway.

A variety of configurations of the distal region 704 are possible to provide varying lateral support for an occlusion that is deeper into a bifurcation junction of an airway. For example, the lateral support regions may further include projections (or wing-like structures) that extend further distally down the airway and provide more distal stenting support.

Figure 9A:
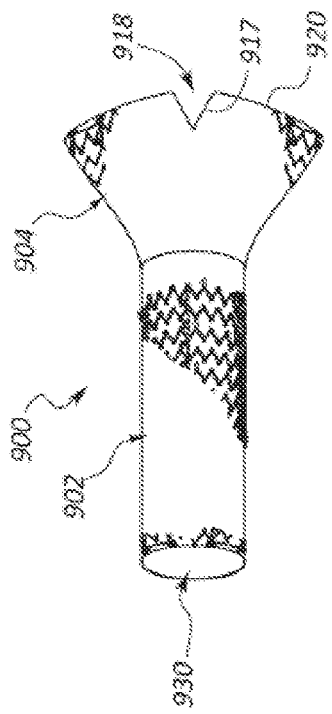
FIG. 9A is a side elevation view of an airway stent, according to another embodiment of the present disclosure.
Figure 9B:
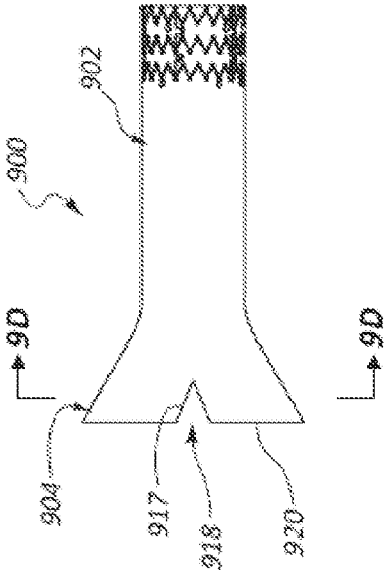
FIG. 9B is a perspective view of the airway stent of FIG. 9A.
Figure 9C:
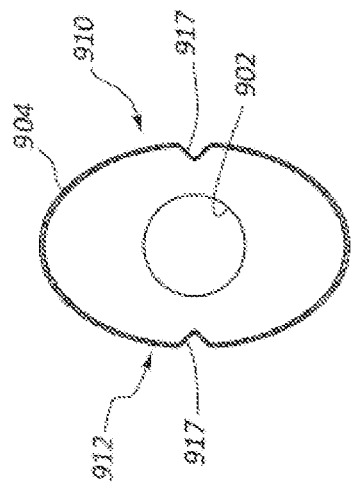
FIG. 9C is another perspective view of the airway stent of FIG. 9A.

FIGS. 9A-9D illustrate an airway stent 900, according to another embodiment of the present disclosure. FIG. 9A is a side elevation view of the airway stent 900. FIG. 9B is a perspective view of the airway stent 900 of FIG. 9A. FIG. 9C is another perspective view of the airway stent 900 of FIG. 9A. FIG. 9C is an end view of the airway stent 900 of FIG. 9A.

The stent 900 of FIGS. 9A-9D may resemble the stent embodiments described above. Accordingly, like features may be designated with like reference numerals, with the leading digits incremented to "9." Relevant disclosure set forth above regarding similarly identified features thus may not be repeated hereafter. Moreover, specific features of the stent 900 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent 900. Any suitable combination of the features and variations of the same described with respect to the previously disclosed stents can be employed with the stent 900, and vice versa. This pattern of disclosure applies equally to further embodiments depicted in subsequent figures and described hereafter.

Referring collectively to FIGS. 9A-9D, the airway stent 900 may include a proximal region 902 (or a mid-body) and a distal region 904 (or a flared region). A non-bifurcated single lumen 930 may be defined through the airway stent 900. The distal region 904 of the airway stent 900 may include a pair of notches 917 in the distal edge 920 that may be configured to engage, for example, the carina 114 (see FIG. 10) of the main bifurcation junction 103 of the trachea 102 or analogous cartilaginous ridge in a more distal bifurcation junction of the airway.

Figure 9D:
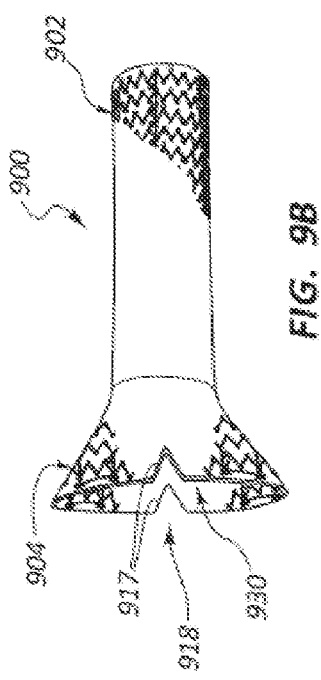
FIG. 9D is an end view of the airway stent of FIG. 9A.

The notches 917 may be positioned opposite each other on the anterior side 910 and posterior side 912 of the distal region 904, as shown in FIG. 9D. The notches 917 may be substantially aligned to form an engagement region 918 at the distal edge 920. The notches 917 and resulting engagement region 918 can provide stability to the positioning of the airway stent 900 by limiting shifting of the stent toward the left or right. The notches 917, by limiting shifting of the stent, reduce a risk that the airway stent 900 may partially occlude the bifurcation junction of the airway. Moreover, the airway stent 900 is substantially secured in place on the carina 114 of the main bifurcation junction 103 (see FIG. 10) or similar cartilaginous ridge of a more distal bifurcation junction, and is thereby limited from migrating distally down the airway. Stabilization of the airway stent 900 at or on the carina 114 (or analogous structure) can provide lateral support for flare region 904 and allow improved stenting expansion to open an occluded bifurcation junction or provide needed structural support of a bifurcation junction.

Figure 10:
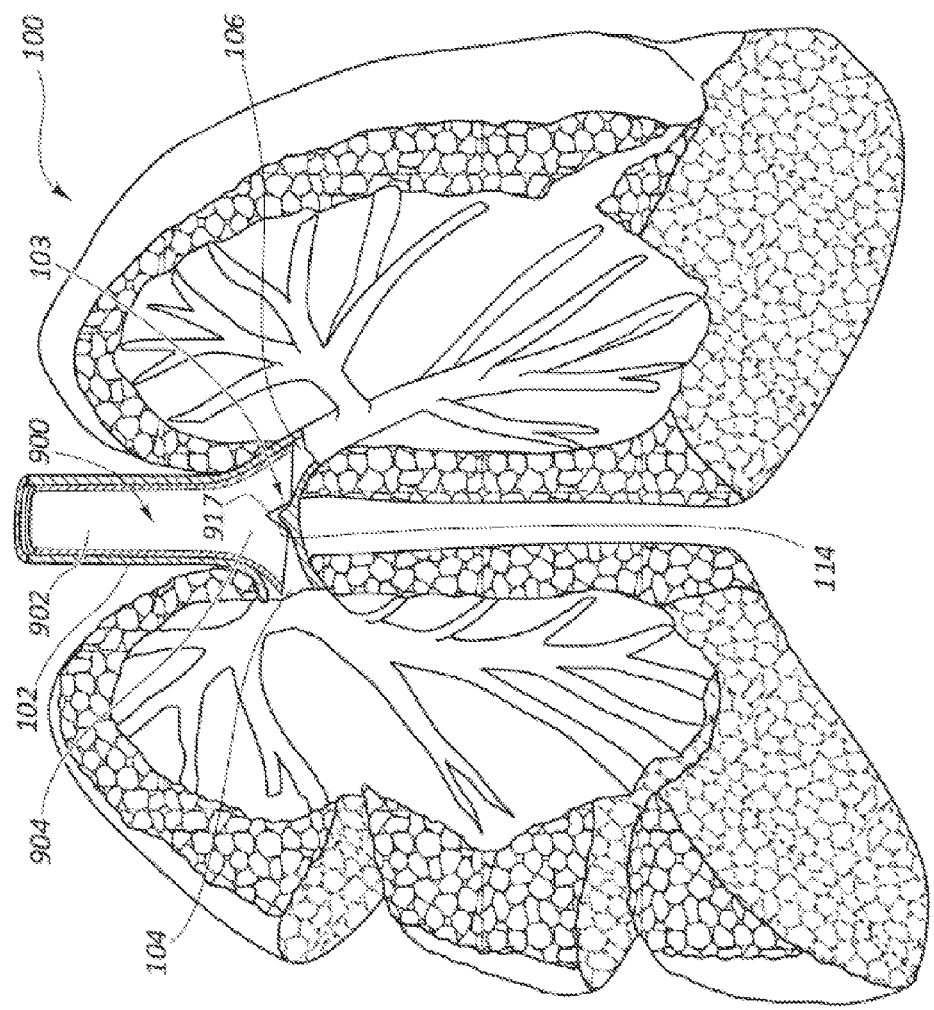
FIG. 10 is a partial sectional view of the airway stent of FIGS. 9A-9D positioned in an airway at the main bifurcation junction.

FIG. 10 is a partial sectional view of the airway stent of FIGS. 9A-9D positioned in an airway to stent the trachea 102 at or near the main bifurcation junction 103, which branches in to the right bronchus 104 and the left bronchus 106. The main body 902 of the stent 900 is disposed within the trachea 102. The distal region 904 is disposed in the main bifurcation junction 103 above (proximal to) the carina 114 and between the right bronchus 104 and the left bronchus 106. The distal region 904 flares and opens into the main bifurcation junction 103. The notches 917 of the distal region 904 are shown engaging the cartilaginous ridge of the bifurcation junction, which in FIG. 10 is the carina 114 in the main bifurcation junction 103.

In another embodiment of an airway stent, a proximal end of the proximal portion may include a flared region. The flared region may be substantially symmetrical. In one embodiment, the flared region at the proximal end may have a diameter that is between one millimeter and four millimeters larger than a diameter of the main-body of the proximal region. The size and degree of the flare region at the proximal end may depend on whether the airway stent is configured for placement in the trachea, bronchi, or bronchioles. The proximal flared region may be a feature of any of the above disclosed embodiments.

The embodiments of the present disclosure may include radiopaque markers at a proximal end and/or a distal stent ends. The markers on the distal end of the stent may be paired at the lateral sides and/or the anterior and posterior sides to aid a practitioner during deployment orientation.

The proximal end may include suture eyelets and/or a suture to aid with purse-string and removal from the airway post deployment.

The examples and embodiments disclosed herein are to be construed as merely illustrative and exemplary, and not a limitation of the scope of the present disclosure in any way. It will be understood to those having skill in the art that changes may be made to the details of the above-described embodiments without departing from the underlying principles of the disclosure herein. For example, any suitable combination of various embodiments, or the features thereof, is contemplated. For example, any of the implantable devices disclosed herein can include a scaffolding structure of any of the other embodiments (e.g., a pattern of strut arms and annular segments of any one or more of the various other disclosed embodiments). As another example, any of the stents can include a distal edge having any of a planar configuration, a concave configuration, or a convex configuration. As another example, any of the stents may include notches in the distal edge. Furthermore, although symmetries are present in the illustrated embodiments, some embodiments may be asymmetrical.

It is intended that the scope of the invention be defined by the claims appended hereto and their equivalents.

What is claimed is:

1. An airway stent, comprising:
a proximal region having a cylindrical shape with a first opening at a proximal end, the first opening having a diameter equivalent to a diameter of the proximal region of the airway stent;
a distal region extending from the proximal region to a second opening at a distal end, the distal region flaring outward such that the second opening has a transverse cross-section with an elliptical shape having a lateral diameter that is larger than an anteroposterior diameter, wherein a distal edge of the distal region includes a first notch at an anterior side and a second notch at a posterior side, wherein the first and second notches are configured to engage a cartilaginous ridge that runs anteroposteriorly between branches of an airway at a target bifurcation junction; and
a non-bifurcated single lumen that extends from the first opening and through the proximal and distal regions to the second opening.

2. The airway stent of claim 1, wherein a transverse cross-section of the non-bifurcated single lumen at a proximal end of the distal region is approximately circular.

3. The airway stent of claim 1, wherein the anteroposterior diameter of the second opening is larger than an anteroposterior diameter of a transverse cross-section of the non-bifurcated single lumen at a proximal end of the distal region.

4. The airway stent of claim 1, wherein the distal region flares outward at a plurality of angles about a circumference of the distal region to conform to an upper surface of an anatomy of a target bifurcation junction of an airway.

5. The airway stent of claim 1, wherein the distal region flares anteroposteriorly at a first angle and flares laterally at a second angle.

6. The airway stent of claim 1, wherein a distal edge of the distal region lies in a plane orthogonal to a longitudinal axis of the non-bifurcated single lumen.

7. The airway stent of claim 1, wherein a distal edge of the distal region is convex as viewed in an anteroposterior direction.

8. The airway stent of claim 1, wherein a distal edge of the distal region is concave as viewed in an anteroposterior direction.

9. The airway stent of claim 1, further comprising a scaffolding structure forming at least a portion of at least one of the proximal region and the distal region and defining a portion of the non-bifurcated single lumen through the airway stent, the scaffolding structure formed of a plurality of annular segments each comprising a plurality of interconnected struts with adjacent struts disposed at angles relative to each other around a circumference of the at least one of the proximal region and the distal region, wherein the plurality of annular segments are arranged in rows in a longitudinal direction of the cylindrical shape.

10. The airway stent of claim 9, further comprising a polymeric cover applied to and between the struts of the plurality of annular segments, the polymeric cover defining an interior region within the scaffolding structure.

11. The airway stent of claim 9, wherein each annular segment of the plurality of annular segments is coupled to an adjacent annular segment.

12. The airway stent of claim 11, wherein the scaffolding structure further comprises a plurality of connectors extending between and interconnecting adjacent annular segments, the connectors arranged in an alternating pattern, such that connectors that are adjacent in the longitudinal direction are offset from each other in a circumferential direction.

13. An implantable device to stent an airway at a bifurcation junction, the implantable device comprising:
a proximal region having a cylindrical hollow tube shape defining a proximal portion of a non-bifurcated single lumen through the implantable device, the non-bifurcated single lumen extending axially along a longitudinal axis of the implantable device from a first opening at a proximal end of the implantable device to a second opening at a distal end of the implantable device;
a distal region disposed at and extending from a distal end of the proximal region, the distal region flaring distally and outwardly from the proximal region to the second opening to define a distal portion of the non-bifurcated single lumen through the implantable device and to enlarge one or more diameters of the non-bifurcated single lumen at the second opening at the distal end of the implantable device, wherein a distal edge of the distal region includes a first notch at an anterior side and a second notch at a posterior side, wherein the first and second notches are configured to engage a cartilaginous ridge that runs anteroposteriorly between branches of an airway at a target bifurcation junction;
wherein the second opening of the non-bifurcated single lumen of the implantable device, at the distal end of the distal region, has a transverse cross-section with an elliptical shape having a first diameter and a second diameter transverse to the first diameter, the first diameter being larger than the second diameter, larger than a diameter of the first opening at the proximal end of the implantable device, and larger than a diameter of a transverse cross-section of the non-bifurcated single lumen at a proximal end of the distal region and at the distal end of the proximal region.

14. The implantable device of claim 13, wherein the anteroposterior diameter of the distal region is larger than an anteroposterior diameter of a transverse cross-section of the non-bifurcated single lumen at a proximal end of the distal region.

15. The implantable device of claim 13, wherein the distal region flares anteroposteriorly at a first angle and flares laterally at a second angle.

16. The implantable device of claim 13, wherein a distal edge of the distal region lies in a plane orthogonal to the longitudinal axis.

17. The implantable device of claim 13, wherein a distal edge of the distal region does not lie entirely in a plane orthogonal to the longitudinal axis.

18. The implantable device of claim 13, further comprising a scaffolding structure forming at least a portion of at least one of the proximal region and the distal region and defining a portion of the non-bifurcated single lumen through the implantable device, the scaffolding structure formed of a plurality of annular segments each comprising a plurality of interconnected struts with adjacent struts disposed at angles relative to each other around a circumference of the at least a portion of the at least one of the cylindrical shape of the proximal region and the distal region, wherein the plurality of annular segments are arranged in rows in the longitudinal direction of the cylindrical shape.

* * * * *